(12) United States Patent
Yamashita et al.

(10) Patent No.: US 7,473,803 B2
(45) Date of Patent: Jan. 6, 2009

(54) PROCESS FOR PRODUCTION OF OPTICALLY ACTIVE 2-HALOGENO-CARBOXYLIC ACIDS

(75) Inventors: Koki Yamashita, Osaka (JP); Toshihiro Takeda, Takasago (JP); Yasuyoshi Ueda, Himeji (JP)

(73) Assignee: Kaneka Corporation, Osaka (JP)

( * ) Notice: Subject to any disclaimer, the term of this patent is extended or adjusted under 35 U.S.C. 154(b) by 409 days.

(21) Appl. No.: 10/503,264

(22) PCT Filed: Feb. 4, 2003

(86) PCT No.: PCT/JP03/01092

§ 371 (c)(1),
(2), (4) Date: Feb. 7, 2005

(87) PCT Pub. No.: WO03/066563

PCT Pub. Date: Aug. 14, 2003

(65) Prior Publication Data

US 2005/0176999 A1    Aug. 11, 2005

(30) Foreign Application Priority Data

Feb. 4, 2002    (JP) .............................. 2002-026579

(51) Int. Cl.
C07C 53/19    (2006.01)
C07B 39/00    (2006.01)
(52) U.S. Cl. ...................................... 562/602; 562/603
(58) Field of Classification Search ........................ None
See application file for complete search history.

(56) References Cited

U.S. PATENT DOCUMENTS

| 4,260,633 A | 4/1981 | Anderson et al. |
| 6,602,866 B2 | 8/2003 | Flynn et al. |
| 2003/0144546 A1 | 7/2003 | Amano et al. |

FOREIGN PATENT DOCUMENTS

| EP | 0 524 553 A1 | 1/1993 |
| EP | 1 138 671 A | 10/2001 |
| EP | 1 422 215 A1 | 5/2004 |
| JP | 56-152451 | 11/1981 |
| JP | 11-80072 | 3/1999 |
| JP | EP 1251115 A1 * | 10/2002 |
| WO | WO 99/42431 | 8/1999 |
| WO | WO 99/55723 | 11/1999 |
| WO | WO 00/40552 | 7/2000 |
| WO | WO 01/55074 A1 | 8/2001 |

OTHER PUBLICATIONS

Gershon, H. et al., "Amino Acid Analogs. 2. 3-Fluoroamino Acids. 1. Chain Length Three to Seven Carbon Atoms," *Journal of Medicinal Chemistry*, 1973, vol. 16, No. 12, pp. 1407-1409.
Johnson, E.P. et al., "Efficient Large Scale Preparation of Neutral Endopeptidase Angiotensin-Converting Enzyme Dual Inhibitor CGS30440," *Organic Process Research & Development*, 1998, 2, pp. 238-244.
International Search Report from Corresponding International Application No. PCT/JP03/01092, Dated May 27, 2003, 4 pages.
Chemical Abstract of Optically Active O-Benzylserines, No. 103828, vol. 94, 1981, p. 795.
Inoue, Hirozumi et al., "A New Enantioselective Synthesis of (2R, 3S)-3-(4-Methoxyphenyl) glycidic Ester via the Enzymatic Hydrolysis of *erythro*-N-Acetyl-β-(4-methoxyphenyl) serine," *Chem. Pharm. Bull.*, vol. 41, No. 9, Sep. 1993, pp. 1521-1523.
Supplementary European Search Report from Application No. EP 03 73 7476, Feb. 3, 2005, 2 pages.

* cited by examiner

*Primary Examiner*—Paul A Zucker
(74) *Attorney, Agent, or Firm*—Brinks Hofer Gilson & Lione

(57) ABSTRACT

The invention provides processes for producing efficiently optically active 2-halogenocarboxylic acids useful in the preparation of drugs or the like and salts thereof with amines. Specifically, an optically active 2-halogenocarboxylic acid is produced by halogenating an optically active amino acid in water in the presence of a hydrophobic organic solvent and nitrous acid with the configuration retained and with the racemization inhibited through the removal of 2-hydroxybromocarboxylic acid formed as a by-product; the obtained optically active 2-halogenocarboxylic acid is transferred to an aqueous phase by converting it into a salt thereof with a base, followed by the removal of the organic phase; and the optically active 2-halogenocarboxylic acid is transferred again to an organic solvent phase, followed by the removal of the aqueous phase, whereby an optically active 2-halogenocarboxylic acid is obtained through the removal of a halogen component. Further, a high-quality salt of an optically active 2-halogenocarboxylic acid with an amine can be obtained by a crystallization method wherein the amine is added over the period of ½ hour or longer either continuously or in portions and/or wherein the crystallization solvent consists of a hydrophobic organic solvent and a hydrophilic organic solvent.

16 Claims, No Drawings

PROCESS FOR PRODUCTION OF OPTICALLY ACTIVE 2-HALOGENO-CARBOXYLIC ACIDS

RELATED APPLICATIONS

This application is a national phase application of PCT/JP03/01092 filed on Feb. 4, 2003, claiming priority from Japanese Patent Application No. 2002-026579 filed on Feb. 4, 2002.

TECHNICAL FIELD

The present invention relates to a process for producing an optically active 2-halogeno carboxylic acid. Particularly, an optically active 2-bromoisovaleric acids, above all, (R)-2-bromoisovaleric acid is a useful compound as an intermediate product for drugs, particularly, ACE/NEP inhibitors (for example, in Organic Process Research & Development (1998), 2, 238-244).

BACKGROUND ART

As a production process for an optically active 2-halogeno carboxylic acid, the following production process has been disclosed, for example, for an optically active 2-bromoisovaleric acid.

Organic Process Research & Development (1998), 2, 238-244, discloses a process of halogenating an optically active valine in water in the presence of a nitrous acid with steric configuration being retained, then extracting the formed optically active 2-bromoisovaleric acid with methyl t-butyl ether, then adding diisopropyl amine thereby forming and, at the same time, crystallizing a diisopropyl amine salt of an optically active 2-bromoisovaleric acid (optical purity of obtained crystals: about 98 to 98.5% ee.)

However, as a result of the studies made by the present inventors, it has been found that the method described above involves the following various problems which give an effect on the quality.

(1) The optical purity of the optically active 2-bromoisovaleric acid obtained is low due to racemization during reaction. Further, it is not always easy to improve the chemical purity and optical purity by purification of the amine salt.
(2) The optically active 2-bromoisovaleric acid tends to be decomposed in successive steps of reaction to crystallization to produce 2-hydroxy carboxylic acid and bromine ingredients as by-products.
(3) The 2-hydroxyisovaleric acid produced as a by-product is difficult to be removed by extraction and tended to accompany as far as final crystallization step.
(4) The bromine ingredients are difficult to be removed in extraction to crystallization and tended to intrude into products.

The foregoing problems give a large burden on the final crystallization step. It is difficult to obtain an optically active 2-halogenocarboxylic acid at high quality in the method described above, and a laborious purification step such as column chromatography or re-crystallization is additionally required for improving the quality.

SUMMARY OF THE INVENTION

In view of the present situations, it is an object of the present invention to overcome the foregoing problems and provide an industrially preferred method for producing a high quality optically active 2-halogenocarboxylic acid. As a result of earnest studies, the present inventors have found that:

(1) racemization can be suppressed drastically in the halogenating reaction carried out in water in the presence of nitrous acid by coexistence of a hydrophobic organic solvent, preferably, a hydrocarbon solvent,
(2) 2-hydroxycarboxylic acid accompanying 2-halogenocarboxylic acid can be removed effectively by using aliphatic hydrocarbon solvents or aromatic hydrocarbon solvents as extraction solvents,
(3) accompanying halogen components can be suppressed by transferring a 2-halogenocarboxylic acid as a salt thereof with a base, preferably, as a metal salt thereof from a liquid extract thereof to an aqueous phase and then transferring the 2-halogenocarboxylic acid again to an organic solvent phase, and
(4) it was found out that crystallizing the optically active 2-halogenocarboxylic acid as an amine salt, preferably, a dialkylamine salt and, more preferably, a dicyclohexylamine salt under specified conditions can give the amine salt at high quality.

Thus, the invention has been achieved.

That is, the present invention relates to a process for producing an optically active 2-halogenocarboxylic acid represented by the general formula (2) (herein also referred to as "an optically active 2-halogeno carboxylic acid (2)"):

(in which R represents an alkyl group which may have a substituent and X represents a halogen atom), which comprises halogenating an optically active amino acid represented by the following general formula (1) (herein also referred to as "an optically active amino acid (1)"):

(in which R represents an alkyl group which may have a substituent) in water in the presence of nitrous acid with the steric configuration being retained, characterized in that racemization is suppressed by co-existence of hydrophobic solvents.

The present invention also relates to a process for producing an optically active 2-halogenocarboxylic acid (2) which comprises extracting, from a reaction solution formed by halogenating an optically active amino acid (1) in water in the presence of nitrous acid with a steric configuration being retained, an optically active 2-halogenocarboxylic acid (2) by an aliphatic hydrocarbon solvent or an aromatic hydrocarbon solvent. The 2-Hydroxy carboxylic acid produced as a by-product can be effectively removed by the operation.

The present invention relates also to a process for producing an optically active 2-halogenocarboxylic acid (2), which comprises halogenating an optically active amino acid (1) in water in the presence of nitrous acid with the steric configuration being retained, to synthesize an optically active 2-halogenocarboxylic acid (2); then transferring a salt of the optically active 2-halogenocarboxylic acid (2) with a base from a liquid extract thereof after the synthesis to an aqueous phase, followed by removal of an organic solvent phase, again neutralizing the salt thereof with the base with an acid to convert into the optically active 2-halogenocarboxylic acid (2); and then transferring the optically active 2-halogenocarboxylic acid (2) to an organic solvent phase, followed by removal of the aqueous phase. The halogen ingredients, particularly, bromine ingredients are effectively removed by the operation.

The present invention further relates to a method of crystallizing a salt of an optically active 2-halogenocarboxylic acid (2) with an amine by adding an amine to the optically active 2-halogenocarboxylic acid (2) continuously or divisionally for ½ hours or more and/or using a hydrophobic organic solvent in combination with a hydrophilic organic solvent as a crystallizing solvent, thereby crystallizing a salt of the optically active 2-halogenocarboxylic acid (2) with an amine. Based on this method an optically active 2-halogenocarboxylic acid (2) at high quality with improved optical purity and chemical purity can be obtained.

Further, the present invention relates to a dicyclohexylamine salt of an optically active 2-halogenocarboxylic acid (2). The amine salt is a novel compound found in the present invention.

DETAILED DISCLOSURE OF THE INVENTION

The present invention is to be described specifically.

In the present invention, an optically active 2-halogenocarboxylic acid (2) is synthesized at first by halogenating an optically active amino acid (1) in water in the presence of nitrous acid with the steric configuration being retained. In a case where the optically active amino acid (1) is used in the (S) form of the conformation, it gives a 2-halogenocarboxylic acid in the (S) form of the conformation predominantly and in a case where the optically active acid (1) is used in the (R) form to give a 2-halogenocarboxylic acid in the (R) form of the conformation predominantly. As the optically active amino acid (1), an (R) form is used more preferably.

In the general formula (2), X represents a halogen atom. Among all, a chlorine atom or a bromine atom is preferred and, particularly, a bromine atom is preferred in view of the high yield of the halogenating reaction and the high reactivity in the reaction of introducing the substituent to the optically active 2-halogenocarboxylic acid (2) at the 2-position.

In the general formulae (1) and (2), R represents an alkyl group which may have a substituent. The alkyl group is an alkyl group containing, usually, 1 to 12 carbon atoms, preferably, 1 to 8 carbon atoms, more preferably, 1 to 6 carbon atoms and, further preferably, 1 to 4 carbon atoms. Specifically, they can include, for example, methyl group, ethyl group, n-propyl group, isopropyl group, isobutyl group, sec-butyl group, tert-butyl group, pentyl group, hexyl group, cyclohexyl group, heptyl group, octyl group, nonyl group, decyl group, undecyl group and dodecyl group. Preferred are isopropyl group and isobutyl group, with the isopropyl group being more preferred.

The substituent for R can include, for example, an alkoxy group containing 1 to 8 carbon atoms such as methoxy group, ethoxy group, t-butyloxy group, and n-octyloxy group; aryloxy group containing 6 to 10 carbon atoms such as phenyloxy group, and p-hydroxyphenyloxy group; benzyloxy group, p-chlorobenzyloxy group; acyl group containing 2 to 10 carbon atoms such as acetyl group and benzoyl group; halogen atoms; hydroxy group, amino group and thiol group.

Halogenation in the present invention is carried out in water. It is particularly preferred to carry out halogenation in an aqueous solution of the optically active amino acid (1). In the halogenation, an organic solvent may coexist with water. The reaction is more preferably carried out in water under the co-existence of a hydrophobic organic solvent. The hydrophobic organic solvent is not limited particularly and can include, preferably, hydrocarbon solvents, ester solvents and ether solvents, the hydrocarbon solvents being used particularly preferably.

The hydrocarbon solvent can include, preferably, aliphatic hydrocarbon solvents and aromatic hydrogen solvents, or halogenated hydrocarbon solvents and, more preferably, aliphatic hydrocarbon solvents or aromatic hydrocarbon solvents.

The aliphatic hydrocarbon solvent is not limited particularly and can include, preferably, aliphatic hydrocarbons containing 5 to 8 carbon atoms, specifically, pentane, hexane, heptan and methylcyclohexane. Among them, aliphatic hydrocarbons containing 6 or 7 carbon atoms, specifically, hexane, heptane and methylcyclohexane are preferred. The aromatic hydrocarbon solvent is not limited particularly and can include, for preferably, aromatic hydrocarbons containing 6 to 8 carbon atoms, specifically, benzene, toluene, and xylene. Among them, aromatic hydrocarbons containing 7 or 8 carbon atoms, specifically, toluene and xylene are preferred. The halogenated hydrocarbon solvent is not limited particularly and can include, preferably, methylene chloride, chlorobenzene, dichlorobenzene and 1,2-dichloroethane. Among them, methylene chloride is preferred.

The ester solvent is not limited particularly and, can include, preferably, acetate esters. The acetate ester can include, preferably, methyl acetate, ethyl acetate, n-propyl acetate and isopropyl acetate. Among them, ethyl acetate is preferred.

The ether solvent is not limited particularly and can include, preferably, acyclic ether solvents. The acyclic ether solvent can include, preferably, methyl t-butyl ether and dibutyl ether. Among them, methyl t-butyl ether is preferred.

The solvent can be used, of course, as a mixed solvent of two or more of them.

The amount of the organic solvent to be used is not limited particularly and the lower limit is usually 0.1 parts by weight, preferably, 0.5 parts by weight and, more preferably, 1 part by weight based on 1 part by weight of the optically active amino acid (1). The upper limit is not limited particularly and it is usually 10 parts by weight, preferably, 5 parts by weight and, more preferably, 3 parts by weight with an economical point of view.

The present reaction can be carried out by using, for example, nitrite, halogenated salt and strong acid, or may also be carried out by using nitrite and hydrogen halide. It is preferably carried out by using the nitrite and hydrogen halide.

The nitrite can include, for example, alkali metal nitrites such as sodium nitrite and potassium nitrite, sodium nitrite being preferred. The strong acid can include inorganic acids such as hydrogen chloride, hydrogen bromide, sulfuric acid, nitric acid or phosphoric acid; and organic acids, for example, organic sulfonic acids such as methane sulfonic acid or benzene sulfonic acid and halogenated organic carboxylic acids such as trifluoro acetic acids. They are preferably inorganic acids and, particularly, hydrogen chloride, hydrogen bromide and sulfuric acid. The halogenated salt can include, for example, alkali metal halides such as lithium chloride, sodium chloride, potassium chloride, lithium bromide, sodium bromide, potassium bromide, lithiumiodide, sodiumiodide, potassiumiodide, sodium fluoride and potassium fluoride.

The hydrogen halide can include, for example, hydrogen chloride, hydrogen bromide, hydrogen iodide and hydrogen fluoride, hydrogen chloride and hydrogen bromide are preferred, and hydrogen bromide is more preferred. The hydrogen halide described above can of course be used as an aqueous solution being dissolved in water (hydrohalic acid).

In a case of using the nitrite, halide salt and strong acid, the amounts of them to be used are not limited particularly. The nitrite is preferably equi-molar or more amount of the optically active amino acid (1), more preferably, the lower limit thereof is usually one mol, preferably, 1.5 mol and, more preferably, 2 mol and the upper limit thereof is usually 5 mol, preferably, 4 mol and, more preferably, 3 mol based on one mol of the optically active amino acids (1). The halide salt is preferably equi-molar or more amount of the optically active amino acid (1), more preferably, the lower limit thereof is usually 2 mol, preferably, 3 mol and, more preferably, 4 mol and the upper limit thereof is usually 20 mol, preferably, 15 mol and, more preferably, 10 mol based on one mol of the optically active amino acids (1). The strong acid is preferably equi-molar or more amount of the optically active amino acid (1), more preferably, the lower limit thereof is usually 2 mol, preferably, 3 mol and, more preferably, 4 mol and the upper limit thereof is usually 20 mol, preferably, 15 mol and, more preferably, 10 mol based on one mol of the optically active amino acids (1).

In a case of using the nitrite and the hydrogen halide, the amounts of them to be used are not limited particularly. The nitrite is preferably equi-molar or more amount of the optically active amino acid (1), more preferably, the lower limit thereof is usually 1 mol, preferably, 1.5 mol and, more preferably, 2 mol, and the upper, limit thereof is usually 5 mol, preferably, 4 mol and, more preferably, 3 mol based on one mol of the optically active amino acid (1). The hydrogen halide is preferably equi-molar or more amount of the optically active amino acid (1), more preferably, the lower limit thereof is usually 2 mol, preferably, 3 mol and, more preferably, 4 mol, and the upper limit thereof is usually 20 mol, preferably, 15 mol and, more preferably, 10 mol based on one mol of the optically active amino acids (1).

The reaction temperature is not limited particularly and the lower limit is usually −20° C. and, more preferably, −10° C., while the upper limit is usually 20° C. and, more preferably, 10° C. Generally, it can be carried out suitably within a range from −10 to 10° C.

In the reaction described above, the nitrite is preferably added to the reaction system while being separated from other ingredients. The addition time of the nitrite is not limited particularly and it is preferred that the lower limit is usually one hour, preferably, 2 hours and more preferably, 3 hours, while the upper limit is usually 20 hours, preferably, 15 hours and, more preferably, 10 hours. The nitrite is suitably used as an aqueous solution (for example, an aqueous 20 to 40 wt % solution of sodium nitrite).

The amount of water to be used in the reaction is not limited particularly and it is usually from 0.1 to 100 parts by weight, preferably, from 0.5 to 50 parts by weight and, more preferably, from 1 to 30 parts by weight based on one part by weight of the optically active amino acid (1), which may be set to an appropriate amount while considering the productivity, the yield and the quality.

In the halogenating reaction described above, the optical purity can be expected usually to be 92% ee, which is enhanced by the co-existence of the hydrophobic organic solvent usually to 97% ee or higher and, preferably, 98% ee or higher. Further, even in a case where the optical purity of the optically active 2-halogenocarboxylic acid (2) obtained by the halogenating reaction described above is lower than 92% ee, the optical purity can be improved usually by 3% ee or higher, preferably, 5% ee or higher and, further preferably, 8% ee or higher by co-existence of the hydrophobic organic solvent.

The resultant optically active 2-halogenocarboxylic acid (2) is extracted from the thus obtained reaction solution to a hydrophobic organic solvent. The hydrophobic organic solvent can include, for example, those described above. It is preferred that the hydrophobic organic solvent used for the reaction also partially or entirely constitutes the extraction solvent but it may also be added separately upon extraction. The hydrophobic organic solvent is preferably the aliphatic hydrocarbon solvent described above or the aromatic hydrocarbon solvent described above. They may be of course used also as the mixed solvent. Extraction of the thus formed optically active 2-halogenocarboxylic acid (2) and removal of 2-hydroxycarboxylic acid produced as a by-product can be carried out efficiently.

Upon extraction by the hydrophobic organic solvent described above, it is preferred to carry out the operation of transferring a salt of the optically active 2-halogenocarboxylic acid (2) with a base, preferably, as a metal salt of the optically active 2-halogenocarboxylic acid (2) (preferably, alkali metal salt such as sodium salt or potassium salt specifically) from the liquid extract of the optically active-halogenocarboxylic acid (2) into an aqueous phase, subsequently, neutralizing the salt thereof with the base with an acid again to convert the same into the optically active 2-halogenocarboxylic acid (2) and transferring the same to an organic solvent phase and removing the aqueous phase. The operation can be carried out once or twice or more. The transfer into an aqueous phase is carried out in a weakly acidic to weakly basic, preferably, weakly acidic to neutral condition, for example, usually at pH from 4 to 8 and, preferably, at pH from 4 to 6. The transfer to an organic solvent phase is carried out in an acidic conditions, for example, usually at pH 2 or less and, preferably, at pH from 0 to 2.

Thus, halogen ingredients, particularly bromine ingredients tending to accompany the optically active 2-halogenocarboxylic acid (2), can be decreased.

As the base, either the inorganic base or the organic base can be used with, but the inorganic base being preferred. While it is not limited particularly, the inorganic base can include specifically, for example, alkali metal hydroxides such as sodium hydroxide and potassium hydroxide; alkali metal carbonates such as sodium carbonate and potassium carbonate; and alkali metal hydrogen carbonate such as sodium hydrogen carbonate, with the alkali metal hydroxide, particularly, sodium hydroxide being preferred. The acid used for the neutralization is not limited particularly and, for example, an inorganic acid such as hydrochloric acid or sulfuric acid can be used suitably.

In the extraction, a washing operation can properly be incorporated, and it is particularly preferred to combine water washing for the extract or organic solvent phase containing the optically active 2-halogenocarboxylic acid (2) (particularly preferably, washing once, twice or more by an aqueous solution (preferably, an aqueous solution from 1% by weight to saturated concentration) of an alkali metal chloride such as sodium chloride, alkali metal sulfate such as sodium sulfate and alkali metal thiosulfate such as sodium thiosulfate, or mixtures thereof), which can assist removal of the impurities.

The thus obtained optically active 2-halogenocarboxylic acid (2) is preferably crystallized as a salt with an amine.

The amine is not limited particularly and can include, for example, ammonia, alkylamine, aralkylamine, aminoacid ester, aminoacid amide, with alkylamine being preferred. The alkylamine can include, for example, monoalkylamine such as isopropylamine and cyclohexylamine; dialkylamine such as diisopropylamine and dicyclohexylamine; trialkylamine such as triethylamine and diisopropylethylamine; and alkylenediamine such as ethylenediamine, trimethylenediamine, tetramethylenediamine, pentamethylenediamine and hexamethylenediamine; with the monoalkylamine and the dialkylamine being preferred and the dialkylamine being more preferred. Use of dicylohexylamine is particularly suitable with a view point of improving the quality.

The amount of the amine to be used is not limited particularly and it is about equi-molar amount based on the optically active 2-halogenocarboxylic acid (2), and the lower limit thereof is usually 0.9 fold-molar, preferably, 0.95 fold-molar and, more preferably, 0.97 fold-molar. While the upper limit thereof is not limited particularly, it is usually 1.2 fold-molar, preferably, 1.1 fold-molar, more preferably, 1.05 fold-molar and, particularly, 1.0 fold-molar with an economical point of view. It can be suitably carried out usually in an amount of from 0.9 to 1.1 fold-molar and, preferably, 0.95 to 1.0 fold-molar.

The crystallizing solvent is not limited particularly and the hydrophobic organic solvents described above, as well as hydrophilic organic solvents, for example, ethers such as THF, dioxane and dimethoxyethane, nitriles such as acetonitrile, ketones such as acetone and lower alcohols such as methanol, ethanol and isopropanol (alcohols containing 1 to 4 carbon atoms) can be used. However, the hydrophobic organic solvent is used preferably as the crystallizing solvent, and it is more preferably a hydrocarbon solvent and, particularly, an aliphatic hydrocarbon solvent. They can include, those described above and those described above are preferred. The solvents described above can be used also as a mixed solvent of two or more of them. Upon crystallization, the extract described above comprising the hydrophobic organic solvent can be used preferably and, as appropriate and more preferably, the extract is concentrated (dewatering under concentration) for improving the yield and the productivity, thereby enabling to increase the crystallization concentration or reduce the water concentration.

For improving the quality of the obtained crystals, it is more preferred to use the hydrophilic organic solvent described above in combination with the hydrophobic organic solvent upon crystallization. In this case, the hydrophilic organic solvent is not limited particularly and those described above can be used. Among all, the lower alcohols described above are particularly preferred and, accordingly, mixed solvents, for example, of the aliphatic hydrocarbon solvent and the lower alcohol, specifically, mixed solvents of the aliphatic hydrocarbon solvent which contains 5 to 8 carbon atoms such as hexane, heptane and methylcyclohexane and the lower alcohol such as methanol, ethanol, and isopropanol can be used preferably. In this case, the amount of the hydrophilic organic solvent to be used is not limited particularly and, as the volume ratio of hydrophilic organic solvent/ (hydrophilic organic solvent+hydrophobic organic solvent), the lower limit is usually 0.05 and, preferably, 0.1 while the upper limit is usually 0.95, preferably, 0.75 and, more preferably, 0.5.

The crystallization method is not limited particularly but the crystallization method can be carried out using any of processes known in the art, such as, for example, a cooling crystallization method, a concentration crystallization method, a crystallization method using solvent substitution, a poor solvent addition method, or a neutralization crystallization method (reaction crystallization method). It is also preferred to properly combine the crystallization methods. A neutralization crystallization method (reaction crystallization method) known so far, that is, a method of adding an amine to the optically active 2-halogenocarboxylic acid (2) thereby crystallizing a salt thereof with the amine can be used particularly preferably. The crystallization is carried out particularly suitably under a deoxidization atmosphere such as an inert gas atmosphere, for example, a nitrogen gas atmosphere for improving quality.

In the neutralization crystallization method (reaction crystallization method), the amine is particularly preferably added by the entire amount for ½ hours or more, preferably, for one hour or more continuously or divisionally.

It is preferred to add seed crystals upon crystallization in order to improve the quality stably by suppression of formation of supersaturation and smooth nucleation.

The crystallization temperature is not limited particularly and it is, usually, 60° C. or lower, preferably, 40° C. or lower and, more preferably, 20° C. or lower and the lower limit is a solidification temperature for the system. Usually, it can be suitably carried out usually about at −20 to 40° C., preferably, −10 to 20° C. In the neutralization crystallization method (reaction crystallization method), it can be carried out usually at 20° C. or lower, preferably, at 10° C. or lower.

Upon crystallization, it is preferred for crystallization under an intense stirring with a power necessary for stirring per unit volume of 0.3 kW/m$^3$ or more, preferably, 0.4 kW/m$^3$ or more and, more preferably, 0.5 kW/m$^3$ or more.

For the salt of the optically active 2-halogenocarboxylic acid (2) with an amine thus obtained, crystals can be collected by-using a general solid/liquid separation method such as centrifugation, filtration under pressure and filtration under reduced pressure. Further, upon collection of crystals, it is also carried out preferably to cool the crystallization solution finally to 10° C. or lower thereby increasing the amount of crystallization. The obtained crystals are optionally further subjected, for example, to drying at a reduced pressure (vacuum drying) and can be obtained as dried crystals.

The present invention is preferably carried out under an inert gas atmosphere such as a nitrogen gas atmosphere for minimizing the decomposition of the optically active 2-halogenocarboxylic acid (2).

Based on the present invention, the optically active 2-halogenocarboxylic acid (2) at high quality can be produced in an industrial scale without requiring recrystallization operation. For the resultant optically active 2-halogenocarboxylic acid (2), it can be expected an optical purity of 99% ee or higher and, preferably, 99.5% ee or higher. Further, also for the chemical purity, it can be expected for 98% or higher and, preferably, 99% or higher.

BEST MODE FOR PRACTICING THE INVENTION

The present invention is to be described more specifically with reference to examples, but the present invention is no way restricted to them.

Quantification and measurement for apparent purity for 2-bromoisovaleric acid and salts thereof, as well as measurement for the content of 2-hydroxyisovaleric acid and bromine ingredients were carried out by using the following analysis system. [Column: manufactured by Nomura Chemical Develosil ODS-HG-3 150 mm×4.6 mm I.D., mobile phase: 0.1 wt/v %, aqueous phosphoric acid/acetonitrile=75/25, flow rate: 1.0 ml/min, detection: UV 210 nm, column temperature: 40° C., retention time: 11.0 min for 2-bromoisovaleric acid, 2.4 min for 2-hydroxy isovaleric acid, 1.8 min for bromine ingredient, 50.0 min for toluene].

The apparent purity for 2-bromoisovaleric acid and salts thereof are represented in the analysis system described above in accordance with the following formula 1:

Apparent purity=(peak area value for 2-bromoisovaleric acid/total for peak area values for detected compounds (excluding solvent peak))×100(%)   (Formula 1)

The content for 2-hydroxyisovaleric acid and bromine ingredient are represented in the analysis system described above in accordance with the following formula 2:

Content=(peak area value for 2-hydroxyisovaleric acid (or bromine ingredient)/total for peak area values for detected compounds)×100(%)   (Formula 2)

Further, the optical purity of 2-bromoisovaleric acid and salts thereof were determined by introducing them into corresponding methyl esters in accordance with the following method and by means of gas chromatographic analysis (GC).

Evaluation of Optical Purity for 2-bromoisovaleric Acid and Salts thereof 20 mg (0.11 mmol) of products was dissolved in a mixed solution of 1 ml of methanol and 3.5 ml of toluene, to which 152 mg (0.14 mmol) of 10% trimethyl silyl diazomethane solution was dropped and, after reacting them at a room temperature for 30 min, the solvent was distilled off under a reduced pressure, and concentrated products were purified on a silica gel column (hexane/ethylacetate=4/1) to obtain methyl 2-bromoisovalerate. The methyl ester was analyzed on gas chromatography (GC) to determine optical purity.

GC Analysis Condition
Column: CP-Chiralsil-Dex CB manufactured by GL Science Co. Inner
diameter: 0.25 mm, length: 25 m, film thickness: 0.25 μm,
Temperature: 60° C. at column, 200° C. at injection port, 220° C. at detector
Detection: FID
Carrier gas: hydrogen and helium (ca.50 kPa)
Retention time: 20.3 min for (S)-2-methyl bromoisovalerate, 22.9 min for (R)-2-methyl bromoisovalerate.

EXAMPLE 1

Preparation of (R)-2-bromoisovaleric Acid 200 g of D-valine was added at an internal temperature of 0° C. to a mixed solution comprising 816 g of 47% hydrobromic acid, 300 ml of water and 300 ml of toluene, cooled to an internal temperature of −5° C. and, successively, a mixed solution of 155.1 g of sodium nitrite and 310 g of water were added for 7 hours. After the completion of addition, they were stirred at an internal temperature of −5° C. for 3 hours (power necessary for stirring per unit volume: 0.2 kW/m$^3$). After adding 500 ml of toluene, temperature was elevated to 20° C. and, after stirring for 1 hour, an organic layer was separated (extract-1). Further, 500 ml of toluene was added to an aqueous layer and, after stirring for 30 min, an organic layer was separated (extract-2). An extract formed by mixing the extract-1 and the extract-2 was washed with 200 ml of an aqueous 20% solution of sodium thiosulfate, 200 ml of a 20% aqueous sodium chloride and then 100 ml of water successively. The thus obtained extract was concentrated under a reduced pressure to obtain 609.4 g of a toluene solution containing 247.22 g of (R)-2-bromoisovaleric acid.

Optical purity 98.1% ee, yield 80%, impurity content 2-hydroisovaleric acid: 0.18%, bromine ingredient: 3.21%.

EXAMPLE 2

Preparation of (R)-2-bromoisovaleric Acid 200 g of D-valine was added at an internal temperature of 0° C. to a mixed solution comprising 816 g of 47% hydrobromic acid, 300 ml of water and 300 ml of hexane, cooled to an internal temperature of −5° C. and, successively, a mixed solution of 155.1 g of sodium nitrite and 310 g of water was added for 7 hours. After the completion of addition, they were stirred at an internal temperature of −5° C. for 3 hours (power necessary for stirring per unit volume: 0.2 kW/m$^3$). After adding 500 ml of hexane, temperature was elevated to 20° C. and, after stirring for 1 hour, an organic layer was separated (extract-1). Further, 500 ml of hexane was added to an aqueous layer and, after stirring for 30 min, an organic layer was separated (extract-2). An extract formed by mixing the extract-1 and the extract-2 was washed with 200 ml of an aqueous 20% solution of sodium thiosulfate, 200 ml of 20% aqueous sodium chloride and 100 ml of water, successively. The thus obtained extract was concentrated under a reduced pressure to obtain 948.8 g of a hexane solution containing 241.0 g of (R)-2-bromoisovaleric acid (Optical purity 96.8% ee, yield 78%, apparent purity 91.3%, impurity content 2-hydroisovaleric acid: not detected, bromine ingredient: 3.24%.

COMPARATIVE EXAMPLE 1

100 g of D-valine was added at an internal temperature of 0° C. to a solution formed by diluting 408 g of 47% hydrobromic acid with 150 ml of water, and cooled to an internal temperature of −5° C. and, successively, a mixed solution of 77.5 g of sodium nitrite and 155 g of water was added for 7 hours. After completion of addition, they were stirred at an internal temperature of −5° C. for 3 hours (power necessary for stirring per unit volume was 0.2 kW/m$^3$). After adding 400 ml of toluene, the temperature was elevated to 20° C. and, after stirring for 1 hour, an organic layer was separated (extract-1). Further, 250 ml of toluene was added to an aqueous layer and, after stirring for 30 min, the organic layer was separated (extract-2). An extract formed by mixing the extract-1 and the extract-2 was washed with 100 ml of an aqueous 20% solution of sodium thiosulfate, 100 ml of 20% aqueous sodium chloride and 50 ml of water successively. The thus obtained extract was concentrated under a reduced pressure to obtain 355.2 g of a toluene solution containing 108.7 g of (R)-2-bromoisovaleric acid (optical purity 92.9% ee. yield 70%, impurity content 2-hydroxy isovaleric acid: not detected, bromine ingredient: 3.74%).

COMPARATIVE EXAMPLE 2

In this comparative example, the result of reaction described in Organic Process Research & Development (1998), 2,238-244 was confirmed.

A mixed solution of 16.0 g of sodium nitrite and 29 ml of water was added at −5° C. for 2.5 hours to a solution comprising 60 ml of 47% hydrobromic acid, 39 ml of water and D-valine. After the completion of addition and after stirring at 0° C. for 1 hour, temperature was elevated to 23° C. and extraction was carried out with 50 ml of methyl t-butyl ether for 3 times. The resultant extracts were mixed and washed with 40 ml of an aqueous 10% solution of sodium thiosulfate, 40 ml of water and 40 ml of aqueous sodium chloride water successively. 22.3 g of (R)-2-bromoisovaleric acid (optical purity 93.5% ee, yield 72%, impurity content 2-hydroxyisovaleric acid: 2.60%, bromine ingredient: 4.67%) was contained in 128.9 g of the thus obtained extract.

EXAMPLE 3

Preparation of (R)-2-bromoisovaleric Acid

After adding 250 g of water to 281 g of a toluene solution of (R)-2-bromoisovaleric acid (containing 115.0 g of (R)-2-bromoisovaleric acid) obtained in Example 1, 76.3 g of an aqueous 30% solution of sodium hydroxide at 5° C. was added to control pH to 4.6, they were successively stirred for 30 min and then separated to obtain an aqueous layer. After washing the resultant aqueous layer with 150 ml of hexane, 650 ml of hexane was added, 60.67 g of concentrated hydrochloric acid was added at 5° C., to control pH to 1.0 and, after stirring for 30 min successively, it was separated to obtain an organic layer (extract-1). Further, 250 ml of hexane was added to the aqueous layer and, after stirring for 30 min at 5° C., it was separated to obtain an organic layer (extract-2). An extract formed by mixing the extract-1 and the extract-2 was washed with 50 ml of 20% aqueous sodium chloride. The thus obtained extract was concentrated to obtain 341.2 g of a hexane solution containing 103.7 g of (R)-2-bromoisovaleric acid (optical purity 98.1% ee, apparent purity 94.8%, impurity content 2-hydroxyisovaleric acid: 0.04%, bromine ingredient: 1.28%).

EXAMPLE 4

Preparation of (R)-2-bromoisovaleric Acid

After adding 400 g of water to 787.4 g of a hexane solution of (R)-2-bromoisovaleric acid (containing 200.0 g of (R)-2-bromoisovaleric acid) obtained in Example 2, 132.2 g of an aqueous 30% solution of sodium hydroxide was added at 5° C. to control pH to 4.6, they were successively stirred for 30 min and then an aqueous layer was separated. After washing the resultant aqueous layer with 200 ml of hexane, 1300 ml of hexane was added, 98.4 g of concentrated hydrochloric acid was added at 5° C., to control pH to 1.2 and, after stirring for 30 min successively, the organic layer was separated (extract-1). Further, 1000 ml of hexane was added to the aqueous layer and, after stirring for 30 min at 5° C., the organic layer was separated (extract-2). An extract formed by mixing the extract-1 and the extract-2 was concentrated to obtain 813.6 g of a hexane solution containing 187.6 g of (R)-2-bromoisovaleric acid (optical purity 96.8% ee, apparent purity 95.7%, impurity content 2-hydroxyisovaleric acid: not detected, bromine ingredient: 0.95%).

EXAMPLE 5

Preparation of (R)-2-bromoisovaleric Acid dicyclohexylamine Salt

To 325.2 g of a hexane solution of (R)-2-bromoisovaleric acid obtained in Example 4 (containing 75.0 g of (R)-2-bromoisovaleric acid), 530.9 g of hexane and 269.7 g of 2-propanol were further added. Seed crystals were added when about ⅔ for 72.5 g of dicyclohexylamine was added continuously for 1.0 hour under a nitrogen atmosphere at 5° C. to crystallize. Further, after continuously adding the remaining about ⅓ for dicyclohexylamine at 5° C. for 0.5 hours, they were stirred at 5° C. for 1 hour. The obtained crystals were filtered under a reduced pressure and then the crystals were washed for 3 times with 150 ml of hexane. The obtained wet crystals were dried under a reduced pressure to obtain 126.45 g of a (R)-2-bromoisovaleric acid dicyclohexylamine salt (optical purity 98.0% ee, crystallization yield 87%, apparent purity 98.9%, impurity content 2-hydroxy isovaleric acid: not detected, bromine content: 0.64%).

$^1$H-NMR (400 MH$_2$, CDCl$_3$) δ (ppm) 1.07 (m, 4H), 1.15-1.28 (m, 6H) 1.53 (m, 4H), 1.64 (m, 2H), 1.78-1.81 (m, 4H), 2.03 (m, 4H), 2.24 (m, 1H), 2.99-3.04 (m, 2H), 4.13 (d, J=6.4 Hz, 1H), IR (KBr) 3059, 2932, 2861, 2635, 2432, 1624, 1581, 1520, 1472, 1455, 1420, 1367, 1302, 1253, 1238, 1186, 1115, 1071, 1036, 976, 916, 899, 887, 855, 839, 764, 706, 654, 594, 561, 492, 447, 405 (cm$^{-1}$).

EXAMPLE 6

Preparation of (R)-2-bromoisovaleric Acid diisopropyl amine Salt

After continuously adding 1.68 g of diisopropylamine under a nitrogen atmosphere at 5° C. for 1 hour to a solution formed by adding 0.79 g of 2-propanol to 12.00 g of a hexane solution of (R)-2-bromoisovaleric acid obtained in Example 3 (containing 3.00 g of (R)-2-bromoisovaleric acid) to crystallize. They were successively stirred at 5° C. for 2 hours. The obtained crystals were filtered under a reduced pressure and then the crystals were washed with 3 ml of a mixed solution of hexane/2-propanol=15/1 (V/V) cooled to 5° C. The obtained crystals were dried under a reduced pressure to obtain 4.35 g of an (R)-2-bromoisovaleric acid diisopropyl amine salt (optical purity 99.1% ee, crystallization yield 93%, apparent purity 98.2%, impurity content 2-hydroxyisovaleric acid: not detected, bromine ingredient: 0.69%).

EXAMPLE 7

To 11.81 g of a toluene solution of (R)-2-bromoisovaleric acid obtained in Example 1 (containing 3.00 g of (R)-2-bromoisovaleric acid), 3.19 g of toluene was further added. After continuously adding 3.00 g of dicyclohexylamine under a nitrogen atmosphere at 5° C. for 1 hour to crystallize. They were successively stirred at 5° C. for 2 hours. The obtained crystals were filtered under a reduced pressure and then the crystals were washed with 3 ml of toluene. The obtained crystals were dried under a reduced pressure to obtain 4.84 g of a (R)-2-bromoisovaleric acid dicyclohexylamine salt (optical purity 99.4% ee, crystallization yield 81%, apparent purity 94.5%, impurity content 2-hydroxy isovaleric acid: 0.04%, bromine content: 3.02%).

COMPARATIVE EXAMPLE 3

In this comparative example, the result of crystallization described in Organic Process Research & Development (1998), 2, 238-244 was confirmed.

After continuously adding 16 ml of diisopropylamine to 128.9 g of a methyl t-butyl ether solution of (R)-2-bromoisovaleric acid obtained in Comparative Example 2 was continuously added at −4° C. for 12 min to crystallize, they were stirred successively at 0° C. for 1 hour. Obtained crystals were filtered under a reduced pressure, and then washed with 30 ml of methyl t-butyl ether. Obtained crystals were dried under a reduced pressure to obtain 27.81 g of (R)-2-bromoisovaleric acid diisopropylamine salt (optical purity 98.1% ee, crystallization yield 80%, apparent purity 92.5%, impurity content 2-hydroxy isovaleric acid; 0.31%, bromine content: 4.58%).

EXAMPLE 8

Preparation of (R)-2-bromopropionic Acid

Concentrated sulfuric acid (16.16 g, 0.16 mol) was slowly added to 110 g of water and, successively, L-alanine (5.90 g, 0.066 mol), KBr (39.4 g, 0.33 mol) and 50 ml of toluene were added successively. The slurry was cooled to −10° C. and sodium nitrite dissolved in 12.9 g of water (7.0 g, 0.10 mol) was added for 2 hours. After stirring at −10° C. over one night, temperature was elevated to a room temperature and the solution was separated. The aqueous layer was discarded and the obtained organic layer was washed twice each with 30 ml of water to obtain a toluene solution of (R)-2-bromopropionic acid. When the optical purity of (R)-2-bromopropionic acid was evaluated by HPLC, it was 76.0% ee.

Evaluation for the optical purity of (R)-2-bromopropionic acid was carried out by using the following analysis system. [Column manufactured by Daicel Chemical [Chiralpak AD 250×4.6 mm}×2 (directly coupled by two), mobile phase: hexane/isopanol/trifluoroacetic acid=95/5/0.1, flow rate: 0.5 ml/min, detection: UV210 nm, column temperature: 10° C., retention time: 29.9 min for (S)-2-bromopropionic acid, 32.7 min for (R)-2-bromopropionic acid].

COMPARATIVE EXAMPLE 4

Preparation of (R)-2-bromopropionic Acid

Concentrated sulfuric acid (16.16 g, 0.16 mol) was slowly added to 110 g of water and, successively, L-alanine (5.90 g, 0.066 mol) and KBr (39.4 g, 0.33 mol) were added successively. The slurry was cooled to −10° C. and sodium nitrite dissolved in 12.9 g of water (7.0 g, 0.10 mol) was added for 2 hours. After stirring at −10° C. over one night, 50 ml of toluene was added, temperature was elevated to a room temperature and the liquid was separated. The aqueous layer was discarded and the obtained organic layer was washed twice each with 30 ml of water to obtain a toluene solution of (R)-2-bromopropionic acid. When the optical purity of (R)-2-bromo propionic acid was evaluated by HPLC, it was 67.0% ee.

EXAMPLE 9

Preparation of (R)-2-bromo-4-methyl valeric Acid

Concentrated sulfuric acid (16.16 g, 0.16 mol) was slowly added to 110 g of water and, successively, L-leucin (8.68 g, 0.066 mol), KBr (39.4 g, 0.33 mol) and 50 ml of toluene were added successively. The slurry was cooled to −10° C. and sodium nitrite dissolved in 12.9 g of water (7.0 g, 0.10 mol) was added for 2 hours. After stirring at −10° C. over one night, temperature was elevated to a room temperature and the liquid was separated. The aqueous layer was discarded and the obtained organic layer was washed twice each with 30 ml of water to obtain a toluene solution of (R)-2-bromo-4-methyl valeric acid. When the optical purity of the (R)-2-bromo-4-methyl valeric acid was evaluated by HPLC, it was 98.0% ee.

Evaluation for the optical purity of (R)-2-bromo-4-methyl valeric acid was carried out by using the following analysis system.

[Column manufactured by Daicel Chemical [Chiralpak AD 250×4.6 mm)×2 (directly coupled by two), mobile phase: hexane/isopropanol/trifluoroacetic acid=95/5/0.1, flow rate: 0.5 ml/min, detection: UV 210 nm, column temperature: 10° C., retention time: 22.3 min for (R)-2-bromo-4-methyl valeric acid, 22.9 min for (S)-2-bromo-4-methyl valeric acid].

COMPARATIVE EXAMPLE 5

Preparation of (R)-2-bromo-4-methyl valeric Acid

Concentrated sulfuric acid (16.16 g, 0.16 mol) was slowly added to 110 g of water and, successively, L-leucin (8.68 g, 0.066 mol) and KBr (39.4 g, 0.33 mol) were added successively. The slurry was cooled to −10° C. and sodium nitrite dissolved in 12.9 g of water (7.0 g, 0.10 mol) was added for 2 hours. After stirring at −10° C. over one night, 50 ml of toluene was added, temperature was elevated to a room temperature and the liquid was separated. The aqueous layer was discarded and the obtained organic layer was washed twice each with 30 ml of water to obtain a toluene solution of (R)-2-bromo-4-methyl valeric acid. When the optical purity of (R)-2-bromo-4-methyl valeric acid was evaluated by HPLC, it was 92.0% ee.

INDUSTRIAL APPLICABILITY

Since the present invention comprises the foregoing constitution, an optically active 2-halogenocarboxylic acids and optically active 2-halogenocarboxylic amine salt important in the production of drugs can be produced economically and efficiently at high optical purity and high chemical purity.

The invention claimed is:

1. A process for producing an optically active 2-halogenocarboxylic acid represented by general formula (2):

comprising halogenating an optically active amino acid represented by general formula (1):

in water in the presence of nitrous acid with the steric configuration being retained, characterized in that the racemization is suppressed by the presence of a hydrophobic organic solvent in the reaction mixture;
wherein R represents an isopropyl group and X represents a bromine atom.

2. The production process according to claim 1 wherein the hydrophobic organic solvent is a hydrocarbon solvent.

3. The production process according to claim 2, wherein the hydrocarbon solvent is an aliphatic hydrocarbon solvent or an aromatic hydrocarbon solvent.

4. The production process according to claim 1, wherein the amount of the hydrophobic organic solvent to be used is 0.1 parts by weight or more based on 1 part by weight of an optically active amino acid.

5. The production process according to claim 1, wherein the halogenating reaction in the presence of nitrous acid is carried out by using a nitrite and a hydrogen halide.

6. The production process according to claim 5, wherein the hydrogen halide is hydrogen bromide.

7. A process for producing an optically active 2-halogenocarboxylic acid represented by general formula (2):

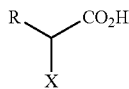
(2)

comprising extracting the optically active 2-halogenocarboxylic acid (2) with an aliphatic hydrocarbon solvent or an aromatic hydrocarbon solvent from a reaction solution formed by halogenating an optically active amino acid represented by general formula (1):

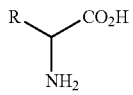
(1)

in water in the presence of nitrous acid with the steric configuration being retained:
wherein R represents an isopropyl group and X represents a bromine atom.

8. The production process according to claim 7, wherein racemization is suppressed by the presence of a hydrophobic organic solvent in the reaction mixture.

9. A process for producing an optically active 2-halogenocarboxylic acid represented by general formula (2):

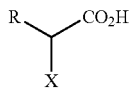
(2)

comprising:
halogenating an optically active amino acid represented by general formula (1):

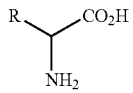
(1)

in water in the presence of nitrous acid with the steno configuration being retained, to synthesize the optically active 2-halogenocarboxylic acid;
transferring a salt of the optically active 2-halogenocarboxylic acid with a base from a liquid extract of the optically active 2-halogenocarboxylic acid after synthesis to an aqueous phase, followed by removal of an organic solvent phase;
neutralizing the salt of the optically active 2-halogenocarboxylic acid with an acid to regenerate the optically active 2-halogenocarboxylic acid; and
transferring the optically active 2-halogenocarboxylic acid to an organic solvent phase, followed by removal of the aqueous phase;
wherein R represents an isopropyl group and X represents a bromine atom.

10. The production process according to claim 9, wherein the salt of the optically active 2-halogenocarboxylic acid with a base is a metal salt of the optically active 2-halogenocarboxylic acid.

11. The production process according to claim 9, wherein the transfer to the aqueous phase is carried out under a weakly acidic to weakly basic condition, and the transfer to the organic solvent phase is carried out under an acidic condition.

12. The production process according to claim 9, wherein the extract and/or the organic solvent phase containing the optically active 2-halogenocarboxylic acid is further washed with water.

13. The production process according to claim 12, wherein the washing with water is carried out with an aqueous solution of an alkali metal chloride, an alkali metal sulfate, an alkali metal thiosulfate, or a mixture thereof.

14. The production process according to claim 9, wherein racemization is suppressed by the presence of a hydrophobic organic solvent in the reaction mixture.

15. The production process according to claim 1, further comprising crystallizing the optically active 2-halogenocarboxylic acid as a salt thereof with an amine by adding an amine continuously or divisionally for ½ hours or more to the optically active 2-halogenocarboxylic acid, and/or by using a hydrophobic organic solvent in combination with a hydrophilic organic solvent as a crystallizing solvent.

16. The production process according to claim 9, further comprising crystallizing the optically active 2-halogenocarboxylic acid as a salt thereof with an amine by adding an amine continuously or divisionally for ½ hours or more to the optically active 2-halogenocarboxylic acid, and/or by using a hydrophobic organic solvent in combination with a hydrophilic organic solvent as a crystallizing solvent.

* * * * *